(12) United States Patent
Kurtz

(10) Patent No.: US 6,856,938 B2
(45) Date of Patent: Feb. 15, 2005

(54) WEIGHT MONITORING COMPUTER

(76) Inventor: Anthony D. Kurtz, 256 Hempstead Rd., Ridgewood, NJ (US) 07450

( * ) Notice: Subject to any disclaimer, the term of this patent is extended or adjusted under 35 U.S.C. 154(b) by 17 days.

(21) Appl. No.: 10/242,244

(22) Filed: Sep. 12, 2002

(65) Prior Publication Data
US 2004/0054497 A1 Mar. 18, 2004

(51) Int. Cl.[7] .................... G01G 11/00; G01G 17/00; G01G 19/00; G01G 7/00; G01G 9/00
(52) U.S. Cl. ................. 702/173; 705/2; 434/127; 434/236; 600/300; 128/921; 364/400; 364/700; 73/379.01
(58) Field of Search ................ 702/173; 705/2; 434/127, 236; 600/300; 128/921; 364/400, 700; 73/379.01

(56) References Cited

U.S. PATENT DOCUMENTS

| | | | | |
|---|---|---|---|---|
| 5,454,721 A | * | 10/1995 | Kuch | 434/127 |
| 5,673,691 A | * | 10/1997 | Abrams et al. | 600/300 |
| 5,839,901 A | * | 11/1998 | Karkanen | 434/127 |
| 5,890,128 A | * | 3/1999 | Diaz et al. | 705/2 |
| 2002/0099274 A1 | * | 7/2002 | Isomura et al. | 600/300 |

* cited by examiner

Primary Examiner—John Barlow
Assistant Examiner—Aditya Bhat
(74) Attorney, Agent, or Firm—Plevy Howard & Darcy, PC

(57) ABSTRACT

There is disclosed a weight reduction computer or a weight monitoring computer, which essentially enables a user to key in the foods consumed during the course of the day and to key in the activities participated in during the course of the day. Both the foods consumed and the activities participated in result in a caloric intake. The amount of calories consumed versus the amount of calories dissipated are automatically computed and an indication is provided to the user indicative of whether or not he is embarking on a successful weight reduction program. The amount of calories dissipated based on the user's exercise are accommodated according to the user's personal data, such as his weight, sex, age and so on. The user can also insert particular activities or foods in the computer, together with their amount of appropriate calories so that the computer can offer personalized data for the user.

20 Claims, 2 Drawing Sheets

| FOOD (Serving) | Calories |
|---|---|
| EGG | CAL. |
| 1 | 100 |
| 2 | 200 |
| 3 | 300 |
| BACON | |
| 1 (slices) | 150 |
| 2 | 300 |
| 3 | 450 |
| CANDY BAR | |
| 1 (choc) | 300 |
| 2 | 600 |

| ACTIVITY | TIME | Calories |
|---|---|---|
| SLEEP | | 40 |
| RUN | | |
| 1 mi | A | 250 |
| 2 mi | B | 600 |
| X | C | |
| SWIM | D | |
| 1 mi | E | 100 |
| 2 mi | F | 300 |
| | G | |
| WALK | H | |

| PERSONAL DATA | |
|---|---|
| WEIGHT | XXX |
| SEX | M - F |
| HGT | XXX |
| AGE | XX |
| PULSE | X/Y |
| Rest | —— |
| FD | —— |
| AD | —— |
| ED | —— |

| ENVIRONMENTAL | |
|---|---|
| TEMP | —— |
| DATE | AA/BB/CC |
| HUMIDITY | —— |
| BREAKFAST | 8  5 |
| LUNCH | 11  1:10 |
| DINNER | 6  9 |
| TIME of DAY | 11:00 PM |

WEIGHT MONITORING COMPUTER

FIELD OF INVENTION

This invention relates to a weight monitoring device and more particularly, to a hand held computer which operates to compute calories consumed and calories dissipated based on food consumption and exercise activities.

BACKGROUND OF THE INVENTION

It is apparent that exercise and diet are paramount in society. Generally, many people in this world are overweight and this should be a concern for them and for their health. Many diets have been implemented which all involve one basic factor, and that is the amount of calories consumed has to be related to the amount of calories dissipated. Thus, if one consumes more calories then one dissipates, then one is going to gain weight and that is a simple fact. While there are many different diets to enable individuals to accommodate their particular needs, there is one general aspect which is prevalent in most diets and that is that you must basically dissipate more calories than you consume. If this occurs, then there is great probability that you are going to lose weight, barring some physiological disturbance.

It is also know that the daily caloric requirements of individuals are effected by many variables, including physical activity, environmental temperature, age, sex, body size and composition. Tables have been constructed of suggested caloric intake for maintaining health according to an individual's weight, height and body type. These tables are well known and widely available.

Reference is made to many publications of the National Research Counsel in Washington, D.C. In any event, it is perfectly clear that calories do count in maintaining health and optimum weight. It also perfectly clear that it is extremely difficult to monitor caloric intake, as well as caloric dissipation, as the average person has very little knowledge of how many calories are contained in various foods and has less knowledge of how many calories are dissipated in various activities. It would be extremely beneficial if one can utilize a simple means to make this determination and therefore, at the end of the day a person would know how to adjust his living habits in regard to how many calories were consumed as compared to how many calories dissipated.

It is an object of the present invention to provide a calculator or computer, which can be handheld or may be implemented on a home computer to enable an average person to determine exactly how many calories were consumed and how many calories were dissipated in a simple and economical manner.

SUMMARY OF INVENTION

A weight monitoring apparatus for an individual user comprises means for enabling a user to enter foods consumed for accumulating a total of calories consumed and means for enabling a user to enter activities performed for accumulating a total of calories dissipated. The apparatus includes means for comparing calories consumed to calories dissipated to provide the user with an indication of whether the user will gain or lose weight in accordance with the comparison.

DETAILED DESCRIPTION OF THE FIGURES

Figures 1, 2, 3, 4, 5:
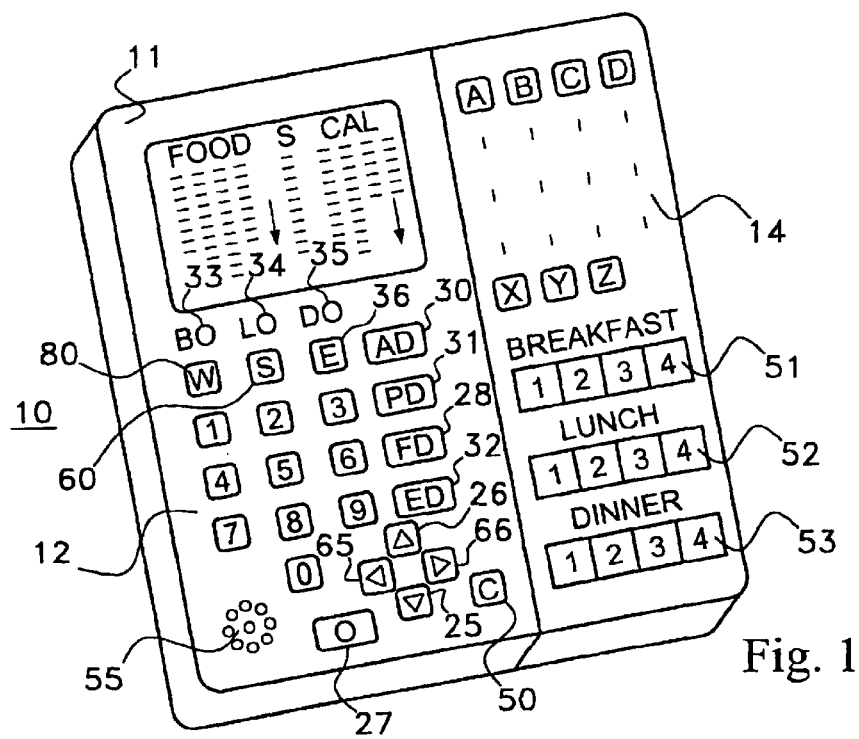
FIG. 1 is a perspective view of a calculator according to this invention.
FIG. 2 is a view of a table of a memory content concerning food and calories utilized in this invention.
FIG. 3 is a table of a memory content showing activity and calories employed in this invention.
FIG. 4 is a table showing personal data of a memory content which is utilized in this invention.
FIG. 5 is a table depicting environmental data for storage in a memory utilized in this invention.

Referring to FIG. 1, there is shown a weight monitoring computer or device 10 according to this invention. It is understood the configuration shown in FIG. 1 is by way of example, and there are many ways of implementing a computer or handheld device according to this invention. It is therefore clear that FIG. 1 is an example of one such implementation and many variations and configurations can be utilized in general. It is also understood that the objectives of this invention can be programmed and implemented on a CD ROM capable of being utilized by a handheld computer, or a PC or other device.

Essentially, the handheld device depicted in FIG. 1 can be referred to as a weight monitoring computer or weight reduction computer. The objective of the computer in FIG. 1 is to enable a person to enter in each day how much food that person consumed and therefore, how many calories were consumed by the individual. The person will also enter in the activities that the person participated in during the day. For example, this activity is associated with calories that the person has utilized in running, swimming or participating in various weightlifting or other exercises. In this manner, a person at the end of a day or during predetermined intervals, will have a good idea of how many calories he consumed versus how many calories were dissipated.

It is, of course, understood that an individual dissipates calories not only during exercise, but while sleeping, eating and other activities. Such indications of calories dissipated in activities during typical exercises are well known and these have been accurately documented. It is also understood that each individual does not dissipate the same amount of calories for the same amount of activity. For example, a person who weighs more will dissipate more calories in doing the same exercise as a person who weighs less. Also, outside temperature would be a factor in determining calories used, as the outside temperature would determine how many calories are dissipated, as well as the weight of the individual, the sex of the individual and so on. The computer 10, as shown in FIG. 1, will enable a user to input this data, as it will be utilized in determining the actual amount of calories dissipated. For example, a male user upon utilizing the calculator will input his personal data as shown, for example, in FIG. 4.

In FIG. 4 the personal data will be received by the calculator in a conventional way. The personal data shown in FIG. 4 is stored in a memory and is used, as will be explained, during processing. The calculator of FIG. 1 contains a microprocessor with various memories, such as read only memories (ROM) and random access memories (RAM) to enable data to be inputted and outputted from the processor shown in FIG. 1. It is, of course, understood that the computer or processor shown in FIG. 1 has a display 11 enabling a user to review various data, which is stored in memory. The computer has a numerical keyboard 12, as well as an alphanumeric keyboard 14, as well as various other keys to enable various functions to be performed. The operation of such keys will be discussed in greater detail. It is the main objective, as indicated, to enable an individual to closely monitor how much an individual consumes in calories and how many calories the individual dissipates. At the end of the day, the processor enables the individual to obtain a count as to whether or not he is consuming more calories than he dissipates and therefore, whether or not his program is going to enable him to lose weight, to gain weight or to maintain his body.

Referring to FIG. 2, there is shown a FOOD and CALORIE table which should be immediately recognized by most individuals who have viewed various texts and diet books. The table in FIG. 2 is indicative of a type of food as shown in the left column, indicated "FOOD", a serving (serving) of the food and the CALORIES. For example, the table shows one egg which constitutes an intake of 100 calories, two eggs which constitutes an intake of 200 calories and three eggs which constitutes an intake of 300 calories. These caloric values are exemplary or fictitious and the actual values can be ascertained and are well known. Similarly, underneath the eggs are bacon, one slice, two slices, three slices, x slices, standing for an arbitrary number of slices. The next list is candy bar, one, two and x, indicating that there are various candy bars. There is shown an arrow in FIG. 2, arrow 21 to ascertain to someone that the food list, as well as calories, can be scrolled. Such lists are well known and the list as depicted in FIG. 2 would be stored in a Read Only Memory, which would be associated with the handheld computer 10 of FIG. 1. Therefore, this memory contains a listing of many typical foods, as one finds in many conventional diet books, together with the calories indicative of each food according to the serving portion. It is quite obvious that if one eats one candy bar, for example, one may consume 600 calories, if one eats four candy bars, one is going to consume 2400 calories and so on. Thus, the storing of a food table, as well as a calorie count and serving portion within the memory located in the handheld computer 10 is implemented. A food table can be derived from many conventional sources and most individuals are fully cognizant of such sources.

As shown, for example in FIG. 1 on display 11, is a listing of the food table depicted in FIG. 2. As one can ascertain, the food appears on the left side of the table, while the calories are on the right side. There are indications in the list that one can utilize the scrolling keys 25 and 26 to scroll up and down the list and therefore, when one reaches a food that one consumes, one can now press button (P) 27 entering the food and then go to the center display servings by using right and left scrolling keys 65 and 66 and again select by the keyboard the portion consumed as the number of units, the number of slices or the number of ounces one has consumed of a particular food.

In any event, the stored food tables and data in the handheld computer enables a user to contain a list of many conventional foods that the average individual consumes, together with the calories and the serving. For example, if a person has two eggs in the morning and two slices of bacon based on the table shown in FIG. 2, there would be the consumption of 500 calories (200+300). As indicated, this is just by way of example and the actual numbers of calories pertaining to the foods are exemplary. The user can also access the memory of FIG. 2 which, for example, may be associated with a Read Only Memory having stored therein conventional tables as depicted. The memory of FIG. 2 can be also implemented together with a Random Access Memory where the individual may place in memory certain foods that are not on the table, but foods that the individual wishes to consume or consumes in his typical diet. Thus, the memory shown in FIG. 2, which is designated as the food and calorie memory is accessible by means of key 28 on the computer entitled "FD". The key 28 labeled "FD" is a food description key and the operation of this key enables a user to add particular foods to be stored. For example, the user depresses key 28 and the display 11 will request that he user enters a food not in the list, as well as a serving portion and caloric content. This information would have to obtained by the user prior to accessing key 28. When the data has been entered using the alphanumeric keyboard 14 and keyboard 12, the user then activates the storage key 60 and the data is now stored in the RAM associated with the food and caloric ROM memory 20 of FIG. 2.

In any event, key 28, when depressed, enables the user to enter the foods that he consumed during desired intervals. Referring to FIG. 3 there is shown another table, which basically is an activity table. The activity table, as stored in memory, is accessed by key 30 shown on the computer of FIG. 1. Basically, the activity table contains a series of events or activities that a typical person would engage in and which are caloric dissipating activities. For example, there is shown the activity "sleep" where an ordinary person dissipates 40 calories sleeping. The activity as running is designated as "RUN" and specified as one mile, two miles, where a person will dissipate 250 in a one-mile run or 600 calories in a two-mile run. Other activities such as swimming for one mile or two miles are also shown, where a person will dissipate other predetermined number of calories according to the activity. There are many activities which would include jogging, fencing, dancing and others, which may be unique to the individual. A unique aspect of the present invention, as will be explained, is that each individual, apart from the tabulated activities, can also enter activities which this person is particularly interested in. For example, a person who is interested in fencing, or some other sport, such as badminton, could obtain calorie information from a conventional source or from an additional book and could place that information in the activity memory, which is a Read Only Memory associated with a Random Access Memory for entering activity data. Again, the activity table is accessed by the "AD" key, which is activity description or AD key 30. Operation is as described for the FD key 28.

Shown in FIG. 4 is an additional table indicated as personal data table. This table in FIG. 4 is again stored in a Random Access Memory, as the data here is particular to the individual. This table is accessed by memory key PD or personal data key 31, as will be further explained. The data, which is stored in the personal data memory, has data indicative of the weight of an individual, the sex of the individual, his height, his age, his rest pulse and also has the indications "FD", "AD" and "ED", which are the food description, the activity description and the environmental description. These descriptions are personal descriptions, where the individual can now indicate the food that he consumes, which is particular to him, as well as activities which are particular to him, as well has some environmental conditions which may be particular to him. As will be seen, these environmental conditions will concern, for example, the time that he eats breakfast, the time he eats lunch and the time he eats dinner so that the computer 10 as shown in FIG. 1 can also activate reminders to enable said individual to be reminded that certain data has not been entered into the system or should be entered into the system.

Referring to FIG. 5, there is shown the environmental data memory, which is accessed by key 32 "ED". Essentially, the environmental data memory stores the temperature, which temperature may be programmed in by the individual or the temperature may be registered by a thermometer or a temperature probe located within the computer of FIG. 1. It also stores the date, similar to a clock. The individual can also enter humidity. More important, there are three items which are designated "breakfast", "lunch" and "dinner". In this manner, the individual enters into the breakfast portion of the memory, the hours which he normally eats breakfast. For example, between 8:00 a.m. and 9:00 a.m., lunch between 11:00 a.m. and 1:00 p.m. and dinner between 6:00 p.m. to 9:00 p.m. This data is entered into memory by means of the keyboard 12 upon prompts given by the computer. One would know exactly how to enter such data and how the computer would be prompted, as will be explained further.

As also seen on the computer are three indicators designated as 33, 34 and 35. These indicators are the "breakfast", "lunch" and "dinner" indicators. The purpose of indicators 33, 34 and 35 is to illuminate after the typical breakfast period has transpired during the course of a day and when no data has been entered by the individual. It serves as a reminder that breakfast data has to be entered for that particular day. If the individual does not want the breakfast data to be entered, he can just press a cancel key, such as key 50, which will extinguish the light. Also shown is a speaker mechanism 55, where the unit can give an audible indication that breakfast data, for example, has not been entered in by the individual and therefore, there is no indication of breakfast data. It is, of course, understood that the tables indicated above are conditioned based on the individual's personal data. For example, when the individual enters personal data such as weight, the activity table shown in FIG. 3 will be modified according to the person's weight. Thus, if, for example, the person weights 200 pounds and is a male, the number of calories which are associated with each activity such as run, swim, walk and so on would be changed accordingly. If the person is a female and weighs 100 pounds, then those figures will also be changed accordingly. In the same way stored values concerning a person's age will also be changed, as older people tend to dissipate more calories when engaged in different exercises. In this manner, as one can ascertain, the computer shown in FIG. 1 is in fact a very accurate device and is indicative of both the intake of calories and the dissipation of calories according to the person's personal data as entered into by the person.

Shown also in FIG. 1 is the alphanumeric keyboard 14, whereby a person can, based on keyboard 14, select a particular food by spelling the food. In other words, if a person consumed an apple, the person would type in APP and apple would appear on display 11 and the number of calories for apple would appear next to it. The person would then press key 28, which would then tell the computer to store those calories because the user consumed an apple. It is also understood that keyboard 14 is not necessary, as one can now just press key 28, label "FD" and enable the food table shown in FIG. 2 to be displayed. One can now use the keys as 25 and 26 to scroll through the key table and to press key 27, which would enable one to select any one of the foods displayed and then depress an enter key, such as key 36 (E), when the proper food is displayed.

Also shown in FIG. 1 are a series of keys as 51, 52 and 53, which are labeled "breakfast", "lunch" and "dinner" and each of these are four keys, for example, under breakfast 1, 2, 3 and 4, label 51, under lunch 1, 2, 3 and 4, label 52 and under dinner, keys 1, 2, 3 and 4 designated as 53. The purpose of these is that an individual may have predetermined breakfasts that he will consume on alternate days, such as, for example, one egg, a piece of bacon, a piece of toast and a cup of coffee. This would be breakfast number one. Instead of accessing each individual food, the individual will press the breakfast key 1 and then key 28. The calories for that particular breakfast will automatically be entered into the computer. In this manner he can do the same for any particular lunch format that he engages in, as well as any particular dinner format. He can also do this and have separate keys for activities and so on. As one can see, the computer arrangement is very versatile, enabling a person to accurately enter the exact foods he eats based on his weight and personal data, as well as the exact activities he engages in based on his personal preferences as well.

Figure 6:
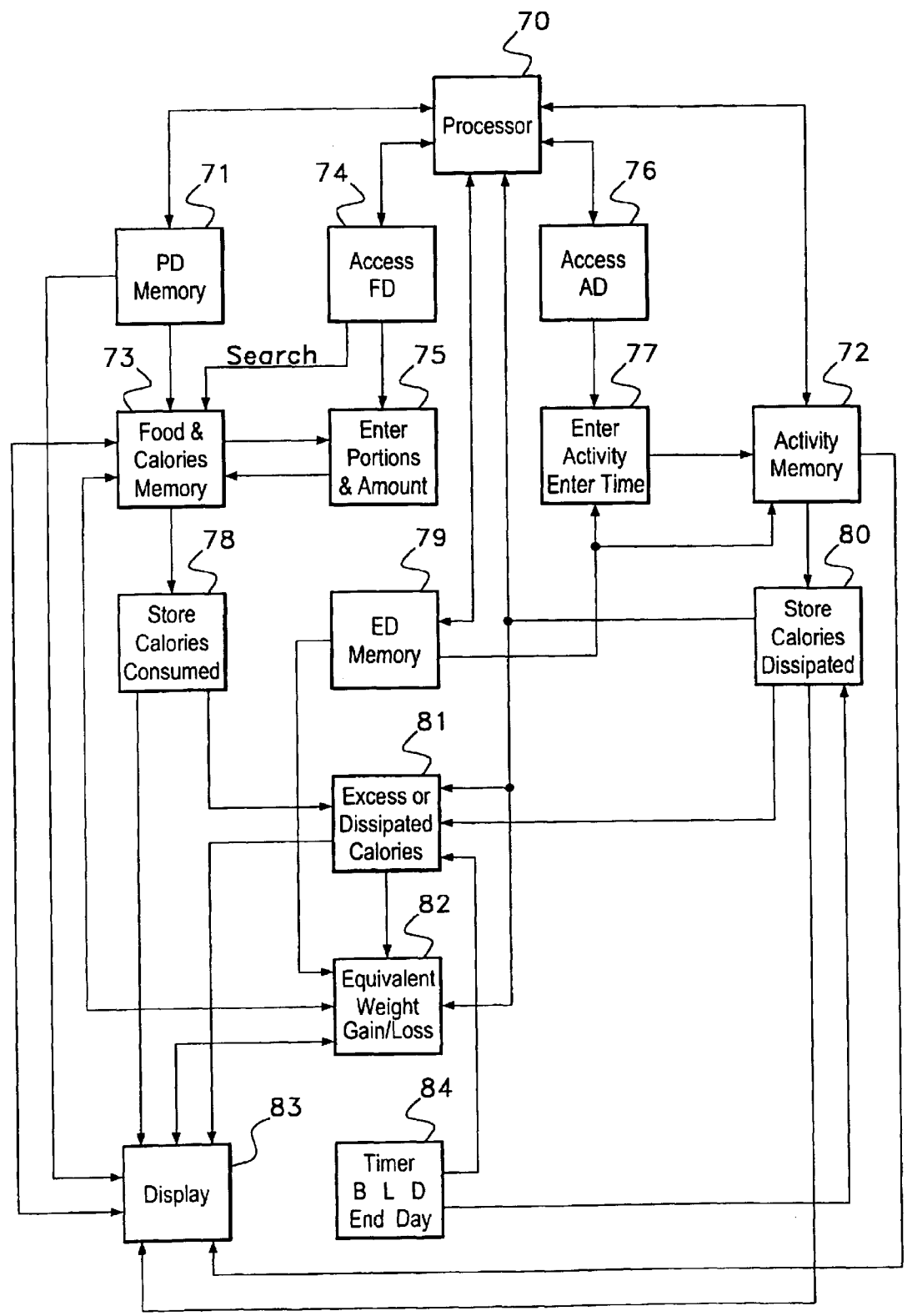
FIG. 6 is a flow chart of an operational sequence for a weight monitoring computer according to this invention.

Referring to FIG. 6, there is shown a block diagram of an operational sequence for the computer shown in FIG. 1. It is noted that in conjunction with FIG. 6, reference will also be made to the tables shown in FIGS. 2, 3, 4 and 5, as well as to the computer configuration shown in FIG. 1. It is, of course, understood that the objective of the invention is to provide a computer apparatus which is simple to utilize and economical to manufacture, which will enable one to get a true understanding of the number of calories consumed compared to the number of calories dissipated based on a person's age, weight, sex, as well as based on environmental conditions. Therefore, one will have a true indication of whether one is consuming more calories than one is dissipating and therefore, is going to gain weight or lose weight. This system works on real time to provide a real time indication of a person's progress in regard to weight reduction.

Referring to FIG. 6, there is shown a processor 70, which essentially is a microprocessor 70 and which accesses most of the memories and devices as previously explained. The microprocessor 70 basically performs computations and calculations based on known techniques and known algorithms, as will be further explained. Essentially, while the microprocessor 70 is shown, it is also indicated that it can perform real time calculations and acts both as an arithmetic unit, as well as having individual storage and access provisions. As one can see from FIG. 6, there is shown the personal data memory 71, which basically is the memory shown in FIG. 4. Hence, when receiving the unit, one depresses the personal data key 31 and then activates, for example, the "set" key 60 shown in FIG. 1. In this manner, on the display are shown the indications of FIG. 4, namely, weight, sex, height, age, pulse and so on. The person then enters the requisite data, such as his weight, his sex, his height, his age and the special data concerning his special foods, special activities and a special environment. When one is finished, one then depressed the "set" key again and this stores that data in the PD memory 71. The PD memory 71 then accesses the processor 70, which goes ahead and accesses the data stored in the activity memory 72 and based on predetermined algorithms, will change the data based on the individual's sex and the individual's weight, for example. In this way the individual data contained in the activity memory 72 would be adjusted for the weight, sex and age of the individual and therefore the caloric count will be changed.

Environmental memory 79 can be accessed by the ED key 32 on the computer. In this manner, when the ED key 32 is depressed, the "set" key 60 will then be depressed. This way the individual can enter data concerning breakfast, lunch and dinner times and when finished can now press the "set" key and therefore enter the data stored in memory. As indicated, the temperature can be stored at real time or an individual can enter the temperature based on his own observations.

The date will be entered and automatically be kept by means of a conventional clock or timer, which is also associated with the computer shown in FIG. 1. The next operation is that the individual, as indicated, will now keep a running track of foods that he has consumed during each meal. Essentially, what would happen is the consumer would press key 28, which would now enable him to access the food description memory 73. Accessing the key 28 is shown in FIG. 6 as step 74. By accessing this key, the first display would indicate calories. As the consumer might exactly know how many calories he did consume and therefore, he does not have to look up any food.

In any event, if no calorie indication is listed, then the display switches to the food and calorie memory and displays the format shown in FIG. 2. The user then scrolls through the various foods and when he comes to the type of food he consumed and the number of units he consumed, he then presses the key 27, which is the "pick" key and therefore, this number of calories is stored in the calorie counter or calorie memory 78, which basically keeps count and track of all food stored. Thus, the user can then, for example, access the memory for breakfast, go to two eggs, which would show 200 calories. By selecting that, 200 calories would go onto the storage 78. Then two slices of bacon, which is 600 calories, would go into the storage 78 as well. In this manner the user can go through this list and select all foods that he ingested for breakfast. One can do this either by accessing the food memory directly, or through the alphanumeric memory 14, the spelling of the foods. For instance, the consumer enters "EG", the display would automatically show "egg" and then the consumer can select the egg by pressing the "P" button, whereby the top selection on each of the displays would be highlighted. The user can scroll the food memory and enter the portion and calories amount as shown in step 75.

After consuming breakfast and entering the various amounts, the processor 70 will know that the consumer has entered the various amounts for breakfast and therefore, the light 33 or the reminder light will not come on. The computer is programmed and tracks the fact that breakfast for the individual is between 8:00 a.m. and 9:00 a.m., for example, and therefore assume that all entries were made between 8:00 a.m. and 9:00 a.m. It is, of course, understood that the entries can be made at any time, as the computer will know that the period of 8:00 a.m. to 9:00 a.m. has passed and no entries have been made, so the breakfast light 33 will remain on until data is entered.

After breakfast the user may take a walk and he may walk a mile. After finishing the walk, he may want to enter that activity into the computer. What the user will do is then access the activity menu. He accesses the activity menu by pressing the AD key 30 of FIG. 1, which is shown in step 76 of FIG. 6. In this manner, he now sees on display 11 the activity menu shown in FIG. 3. He can now scroll the memory and, for example, go to the "walk" column where he can now press the "P" key and enter in the activity, for example, "I walked one mile". This is indicated by entering the activity and time shown in step 77. This would be associated with a definitive number of calories, which are now transferred from the activity memory to the store calorie dissipated counter 80. For example, a one-mile walk may be equivalent to the dissipation of 150 calories, or 150 calories will now be stored in the "calories dissipated" storage. If the consumer wanted a read out of how many calories he consumed, he would press the "W" key 80 shown in FIG. 1. The "W" key 80 basically causes a display of the difference in calories consumed and dissipated. This is shown in module 81 of FIG. 6, which is indicated excess or dissipated calories. The number of calories, whether it is positive or negative, would be displayed on display 83. Therefore, the user would know that, for example, after breakfast he has a plus indication, which means he has consumed more calories than dissipated.

It is also shown in FIG. 6 via module 82 that based on the user's size and weight and the number of calories dissipated or consumed can be converted into the equivalent of weight gained or lost. For example, one can correlate the number of calories to the amount of weight which a user would gain or lose considering whether the calories are positive or negative. This is also a well known calculation and can be easily implemented, as shown in module 82 with help of the processor 70. Also shown is the timer module 84, which basically receives data from the personal memory 71 through the processor and now can indicate by reviewing the personal data memory as to whether breakfast, lunch and dinner have ended and whether or not the proper data has been stored. Basically, timer 84 is a clock which keeps track of time of day, as well as days in the week and so on. At the end of the day, the timer can indicate the exact calories dissipated or exceeded during that day and therefore, the timer 84 activates module 81 to cause the display 83 to determine the amount of calories that the consumer has dissipated or exceeded for that given day. This can occur, for example, at 10:00 p.m. every night and can be set by the user in regard to the personal data memory or the environmental memory as shown in FIG. 5.

Essentially, as one can ascertain, the above-noted system simply computes the calories that a person consumes versus the calories that a person dissipates and then provides a reading of the calories to enable a person to keep track of whether or not he is losing or gaining weight. The system also enables one to determine with great accuracy the calories in various foods, which may be useful for the purposes of dieting, although the main aspect is to take calories consumed by the servings of food and subtract them from calories dissipated during activities. The calories dissipated are computed by means of the processor to take into consideration the personal data indicative of the particular individual, as well as the environmental data. The unit gives signals to the person as to whether or not data has been entered indicative of breakfast, lunch and dinner which are, of course, the main meal times. It would be up to the individual to submit caloric content during the course of the day. For example, the person may decide to eat a chocolate bar or other type of condiment. Therefore, the person would have to access the food key 28 and access the particular item on the food table and select that so the proper number of calories are stored in the calorie counter 78.

It is also indicated that the unit has fixed keys, so that a person who eats the same breakfast during various days can press a fixed key shown in FIG. 1 by reference numeral 51. One can process a fixed lunch by pressing a fixed key as shown by numeral 52 and so on. The unit depicted in FIG. 1 can be extremely small and, for example, can be no larger than a typical handheld computer or handheld calculator such as a Palm Pilot or other device. While the unit in FIG. 1 shows both a numerical keyboard and an alphanumerical keyboard, it is understood that just a numerical keyboard such as a telephone keyboard with various letters can also be employed. The unit can also be voice activated, as one can ascertain. It is the main aspect of the unit to enable one to monitor calorie intake, as well as calories dissipated according to a person's own personal data, such as age, weight and so on to gain an accurate indication of whether this person is embarking on an effective weight reduction program or not.

It should be clear to those skilled in the art that there are many alternate embodiments, which are, of course, ascertained to be accommodated within the spirit and scope of the claims appended hereto.

What is claimed is:

1. A weight monitoring apparatus for an individual user comprising:
   means for enabling a user to enter foods consumed for accumulating a total of calories consumed,
   means for storing environmental data to enable said user to define the time periods during which the user consumes meals, wherein said weight monitoring apparatus further comprises means for alerting the user if the user fails to enter the foods consumed during the defined times for the meals;
   means for enabling said user to enter activities performed for accumulating a total of calories dissipated, and
   means for comparing calories consumed to calories dissipated to provide said user with an indication of whether the user will gain or lose weight in accordance with said comparison.

2. The weight monitoring apparatus according to claim 1 including:
   memory means for storing a list of food items and the caloric content for each item, including means for storing a list of activities which are performed by individuals and the caloric dissipation for each activity performed.

3. The weight monitoring apparatus according to claim 2 further including:
   display means coupled to said memory means to enable a user to display said food items and the caloric content for the food displayed and means for selecting a displayed food item indicative of a consumed food.

4. The weight monitoring apparatus according to claim 2 further including:
   means coupled to said display means and said memory to enable said list of activities to be displayed, including means for selecting a displayed activity to enable said user to select activity performed to add to said calories dissipated.

5. The weight monitoring apparatus according to claim 1 further including:
   means for storing personal data indicative of said user to enable accurate weight monitoring, including at least one of the following data: weight, sex, age, height, pulse rate.

6. The weight monitoring apparatus according to claim 1 wherein said means for storing environmental data further includes means to enable accurate weight monitoring, including at least one of the following data, temperature, humidity or time of day.

7. The weight monitoring apparatus according to claim 1 further including:
   means for selecting predetermined food combinations indicative of calories consumed for a given repeated meal.

8. The weight monitoring apparatus according to claim 4 further including:
   a processor coupled to said memory means and responsive to said items entered by said user to provide an indication of weight gained or lost for a given period of time.

9. The weight monitoring apparatus according to claim 1 wherein said means for enabling a user to enter activities includes a keyboard for entering activity data.

10. The weight monitoring apparatus according to claim 8 wherein said processor is operative to modify said calories dissipated according to said stored personal data.

11. The weight monitoring apparatus according to claim 1 including:
    alarm means operative to notify a user at given intervals reminding said user to insert data indicative of food consumed.

12. A weight monitoring apparatus for an industrial user comprising:
    a processor including a main memory for storing a list of food items and the caloric content for a serving of each item, said memory including means for storing a list of activities which may be performed by said user and the caloric dissipation for each activity performed and including means for storing personal data indicative of said user,
    means coupled to said processor for enabling a user to enter foods consumed for accumulating a total of calories consumed by accessing said list of foods and selecting foods on said list as consumed by said user, and the calories absorbed with said consumed food,
    means for storing environmental data to enable said user to define the time periods during which the user consumes meals, wherein said weight monitoring apparatus further comprises means for alerting the user if the user fails to enter the foods consumed during the defined times for the meals;
    storing in a first memory said calories associated with said consumed foods,
    means coupled to said processor for enabling a user to enter activities performed by said user by selecting said activity from said stored list and the caloric dissipation associated with said activity,
    storing in a second memory said calories associated with said activity,
    means for subtotaling the contents of said first memory with the contacts of said second memory to provide a weight indication of whether said individual has consumed or dissipated calories indicative of a potential weight gain or loss.

13. The weight monitoring apparatus according to claim 12, further including:
    means responsive to said personal data stored to modify caloric dissipation for said activities according to said stored personal data.

14. The weight monitoring apparatus according to claim 13 wherein said personal data includes data regarding said users, sex, weight, height and age.

15. The weight monitoring apparatus according to claim 12 further including,
    means coupled to said processor to enable a user to access said list of food items to add preferred items to said list according to user preference.

16. The weight monitoring apparatus according to claim 12 further including:
    means coupled to said processor to enable said user to access said list of activities to add to said list an activity preferred by said user.

17. The weight monitoring apparatus according to claim 16 further including:
    timing means coupled to said processor for indicating time of day.

18. The weight monitoring apparatus according to claim 17 including means coupled to said timing means for prompting said user to enter foods consumed and activities participated in during desired intervals.

19. The weight monitoring apparatus according to claim 12 further including means responsive to said user individual data and said weight indication to convert said indication into a unit of weight that said individual may gain or lose accordingly to said indication.

20. The weight monitoring apparatus according to claim 12 further including a display coupled to said processor and objective to display the content of said main memory as selected by said user.

* * * * *